United States Patent
VanBlon et al.

(10) Patent No.: US 11,291,411 B2
(45) Date of Patent: Apr. 5, 2022

(54) AUTOMATIC ADJUSTMENT OF WEARABLE DEVICE BAND

(71) Applicant: Lenovo (Singapore) Pte. Ltd., Singapore (SG)

(72) Inventors: Russell S. VanBlon, Raleigh, NC (US); Robert J. Kapinos, Durham, NC (US); Timothy W. Kingsbury, Cary, NC (US); Scott W. Li, Cary, NC (US)

(73) Assignee: Lenovo (Singapore) Pte. Ltd., Singapore (SG)

( * ) Notice: Subject to any disclaimer, the term of this patent is extended or adjusted under 35 U.S.C. 154(b) by 238 days.

(21) Appl. No.: 15/925,598

(22) Filed: Mar. 19, 2018

(65) Prior Publication Data

US 2019/0282166 A1 Sep. 19, 2019

(51) Int. Cl.
| | |
|---|---|
| *A61B 5/00* | (2006.01) |
| *A61B 5/11* | (2006.01) |
| *H04W 4/029* | (2018.01) |
| *A44C 5/24* | (2006.01) |

(52) U.S. Cl.
CPC ............ *A61B 5/6824* (2013.01); *A44C 5/246* (2013.01); *A61B 5/1118* (2013.01); *H04W 4/029* (2018.02)

(58) Field of Classification Search
CPC .................................................. A61B 5/1118
See application file for complete search history.

(56) References Cited

U.S. PATENT DOCUMENTS

| | | | |
|---|---|---|---|
| 10,455,906 B1* | 10/2019 | Wu ........................ A44C 5/027 |
| 2008/0171915 A1* | 7/2008 | Kawajiri ............ A61B 5/02241 600/300 |
| 2013/0053661 A1* | 2/2013 | Alberth ................ A61B 5/1455 600/322 |
| 2014/0070042 A1* | 3/2014 | Beers ...................... A61F 5/028 242/413 |
| 2014/0206948 A1* | 7/2014 | Romem ............... A61B 5/0022 600/301 |
| 2014/0335490 A1* | 11/2014 | Baarman .............. A61B 5/0022 434/236 |
| 2015/0118669 A1* | 4/2015 | Wisbey ................ A61B 5/4866 434/247 |
| 2016/0228066 A1* | 8/2016 | Szabados ........... A61B 5/02055 |
| 2016/0255944 A1* | 9/2016 | Baranski .............. A44C 5/0069 |
| 2017/0086742 A1* | 3/2017 | Harrison-Noonan ........................ A61B 5/6831 |
| 2017/0290553 A1* | 10/2017 | Matsudaira ............ A61B 5/742 |
| 2018/0338721 A1* | 11/2018 | Wang .................... A61B 5/7221 |
| 2020/0375506 A1* | 12/2020 | Bishop ............... B65H 75/4486 |

* cited by examiner

*Primary Examiner* — Rex R Holmes
*Assistant Examiner* — Jennifer L Ghand
(74) *Attorney, Agent, or Firm* — VanLeeuwen & VanLeeuwen; Jason A. Friday (57) ABSTRACT

An approach is provided that automatically adjusts a band of a wearable electronic device. The approach detects conditions, such as activity-based conditions and location-based conditions, and automatically adjusts the band of the wearable electronic device based on the detected conditions.

11 Claims, 6 Drawing Sheets

AUTOMATIC ADJUSTMENT OF WEARABLE DEVICE BAND

BACKGROUND

Traditional wearable devices slide on the user's arm or become too tight for various reasons. This causes the user discomfort, movement of the device, and/or bad fitness readings from the device. A proper fit is desired for wearable devices. In addition, with traditional implementations, wearable fitness bands become dirty and damaged over time due to the user's perspiration and over-tightening of the band to prevent slippage of the device while the user is engaged in more strenuous activities. Traditional wearable devices can be adjusted by the user, but this requires manual adjustment which might not be possible based upon the activity in which the user is engaged, such as during a strenuous game of tennis.

SUMMARY

An approach is provided that automatically adjusts a band of a wearable electronic device. The approach detects conditions, such as activity-based conditions and location-based conditions, and automatically adjusts the band of the wearable electronic device based on the detected conditions.

The foregoing is a summary and thus contains, by necessity, simplifications, generalizations, and omissions of detail; consequently, those skilled in the art will appreciate that the summary is illustrative only and is not intended to be in any way limiting. Other aspects, inventive features, and advantages will become apparent in the non-limiting detailed description set forth below.

BRIEF DESCRIPTION OF THE DRAWINGS

This disclosure may be better understood by referencing the accompanying drawings, wherein.

DETAILED DESCRIPTION

An approach is depicted in FIGS. 1-6 that describes a wearable device with an automatically adjustable band based on factors, such as the user's current activity or the user's current location. This approach automatically determines the amount a wearable device band should be tightened or loosened based on one or more of the following. First, the device band is tightened or loosened when the user's arm in a certain orientation with the tightening performed to keep the band from sliding down when the user's arm is vertical. This allows the device band to fit more loosely when the arm is horizontal and the watch is less likely to slide. When the user's arm is vertical, the band is automatically tightened to stay in position due to effect of gravity. Second, the approach detects when the wearable device band is moist or the user is perspiring. The device band is less likely to slide when the user's arm is "stickier" from perspiration or dampness. A hygrometer or galvanometer is used to detect the moisture level of the user's arm by measuring bioelectric impedance of the user's skin surface. Third, the approach detects a high level of wearable movement and adjusts the device band accordingly.

The movement would be different and could be specific based on the activity being performed by the user (e.g., playing tennis, golf, basketball, running, working out at a gym, etc). In one approach, the system tightens the device band in order to receive a better heart rate reading while the user is performing an activity. The activity being performed be manually input by the user, or automatically predicted by the system based on the user's current location assuming that such data is available (e.g. user is on a basketball court, baseball field, tennis court, track, golf course, etc). Fourth, once periodic activity is known (based on historical exercise at a time/date, location, or nearby devices/friends), the system can preemptively adjust the band based on the activity that is expected to be performed. For example, the system can tighten when the user is proximate to tennis courts or just before the user is expected to start exercising.

A combination of the above could be factored in when deciding automatic band adjustment. For example, the system can periodically loosen the band when high moisture is detected so the band can air out, but only when the arm is expected to be in an extended horizontal position (e.g. while typing on a keyboard, etc.). In addition, the approach can be configured to only do the "air out" of the band when exercise is not expected. There are several benefits of this approach. First, the band would be more comfortable by not over-tightening the band unless necessary, and the band would not feel as "sticky" as with traditional approaches. Second, the band would not slide up and down the user's wrist/arm to an undesired position. And, third, the band would last longer between cleanings.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The detailed description has been presented for purposes of illustration, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

As will be appreciated by one skilled in the art, aspects may be embodied as a system, method or computer program product. Accordingly, aspects may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present disclosure may take the form of a computer program product embodied in one or more computer readable medium(s) having computer readable program code embodied thereon. Logic as used herein include actions and self-contained sequence of actions to be performed by digital circuits characterized by the technology underlying its logic gates as well as by one or more processors programmed to execute instructions that perform such actions.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device. As used herein, a computer readable storage medium does not include a computer readable signal medium. In other words, a computer readable storage medium only includes tangible media upon which the computer instructions are stored and does not include any non-tangible media.

Computer program code for carrying out operations for aspects of the present disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present disclosure are described below with reference to flowchart illustrations and/or block diagrams of methods, apparatus (systems) and computer program products. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The following detailed description will generally follow the summary, as set forth above, further explaining and expanding the definitions of the various aspects and embodiments as necessary. To this end, this detailed description first sets forth a computing environment in FIG. 1 that is suitable to implement the software and/or hardware techniques associated with the disclosure. A networked environment is illustrated in FIG. 2 as an extension of the basic computing environment, to emphasize that modern computing techniques can be performed across multiple discrete devices.

Figure 1:
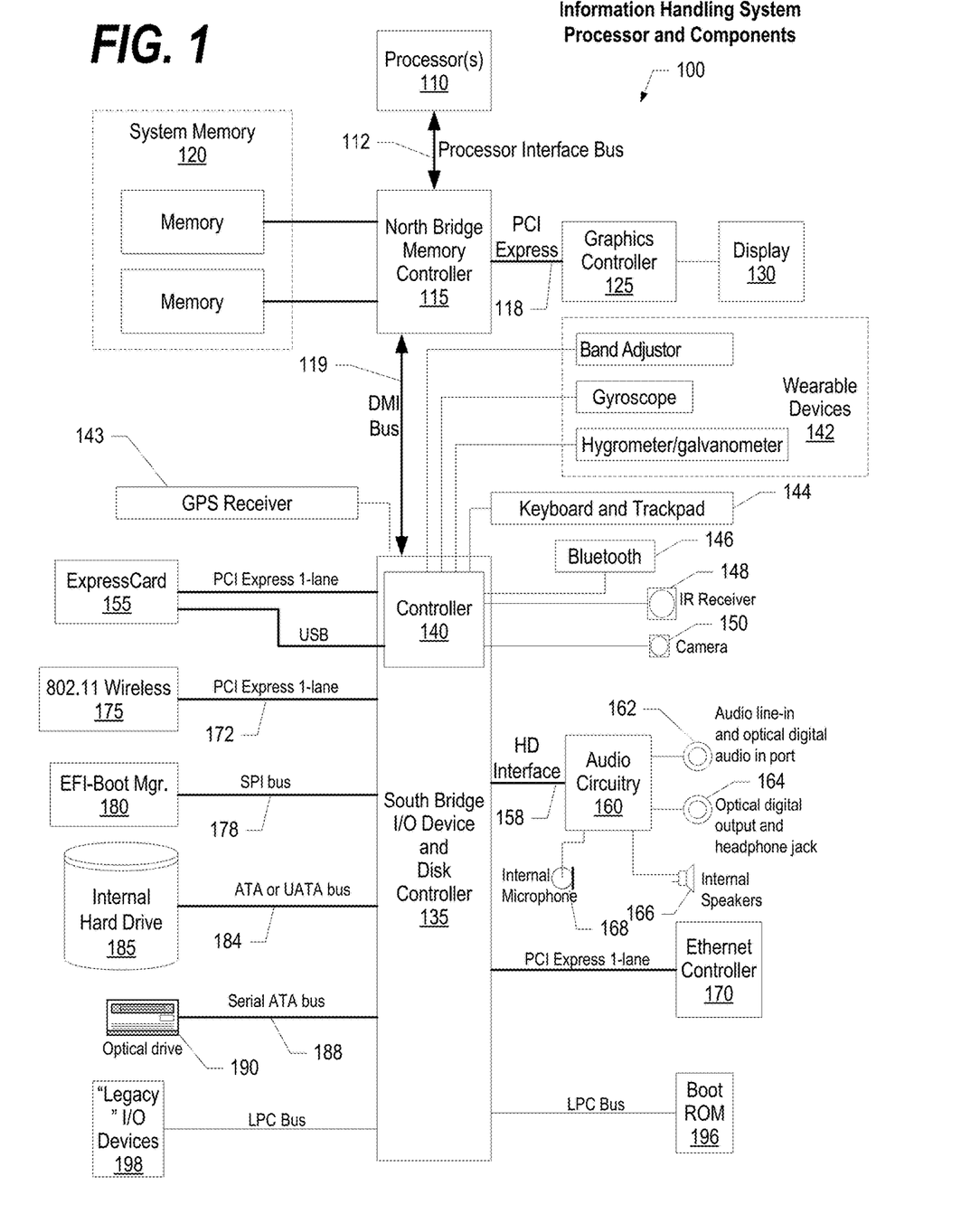
FIG. 1 is a block diagram of a data processing system in which the methods described herein can be implemented.
Figure 2:
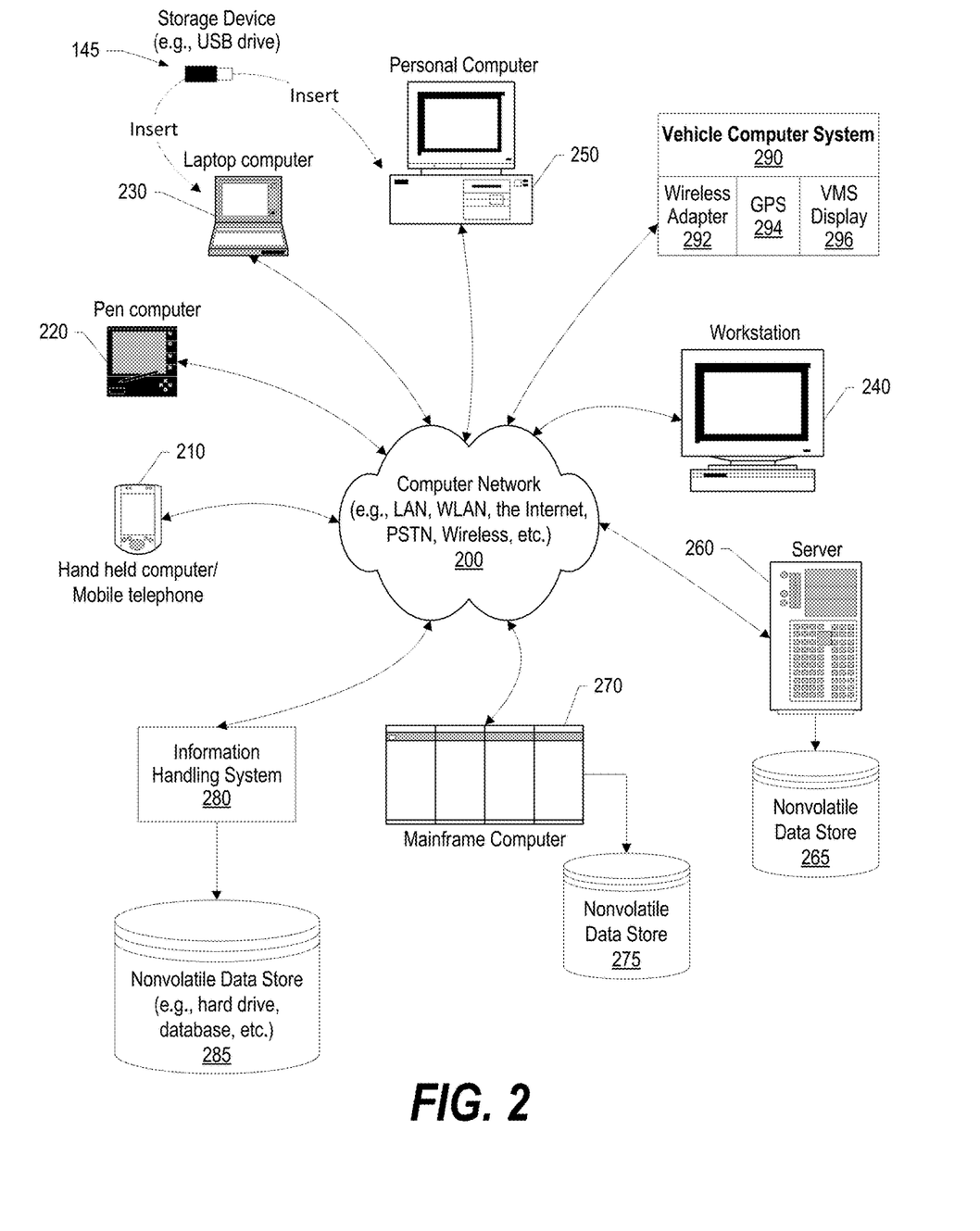
FIG. 2 provides an extension of the information handling system environment shown in FIG. 1 to illustrate that the methods described herein can be performed on a wide variety of information handling systems which operate in a networked environment.

FIG. 1 illustrates information handling system 100, which is a simplified example of a computer system capable of performing the computing operations described herein. Information handling system 100 includes one or more processors 110 coupled to processor interface bus 112. Processor interface bus 112 connects processors 110 to Northbridge 115, which is also known as the Memory Controller Hub (MCH). Northbridge 115 connects to system memory 120 and provides a means for processor(s) 110 to access the system memory. Graphics controller 125 also connects to Northbridge 115. In one embodiment, PCI Express bus 118 connects Northbridge 115 to graphics controller 125. Graphics controller 125 connects to display device 130, such as a computer monitor.

Northbridge 115 and Southbridge 135 connect to each other using bus 119. In one embodiment, the bus is a Direct Media Interface (DMI) bus that transfers data at high speeds in each direction between Northbridge 115 and Southbridge 135. In another embodiment, a Peripheral Component Interconnect (PCI) bus connects the Northbridge and the Southbridge. Southbridge 135, also known as the I/O Controller Hub (ICH) is a chip that generally implements capabilities that operate at slower speeds than the capabilities provided by the Northbridge. Southbridge 135 typically provides various busses used to connect various components. These busses include, for example, PCI and PCI Express busses, an ISA bus, a System Management Bus (SMBus or SMB), and/or a Low Pin Count (LPC) bus. The LPC bus often connects low-bandwidth devices, such as boot ROM 196 and "legacy" I/O devices (using a "super I/O" chip). The "legacy" I/O devices (198) can include, for example, serial and parallel ports, keyboard, mouse, and/or a floppy disk controller. The LPC bus also connects Southbridge 135 to Trusted Platform Module (TPM) 195. Other components often included in Southbridge 135 include a Direct Memory Access (DMA) controller, a Programmable Interrupt Controller (PIC), and a storage device controller, which connects Southbridge 135 to nonvolatile storage device 185, such as a hard disk drive, using bus 184.

ExpressCard 155 is a slot that connects hot-pluggable devices to the information handling system. ExpressCard 155 supports both PCI Express and USB connectivity as it connects to Southbridge 135 using both the Universal Serial Bus (USB) the PCI Express bus. Southbridge 135 includes USB Controller 140 that provides USB connectivity to devices that connect to the USB. These devices include digital camera 150, optical distance sensor 148, keyboard and trackpad 144, and Bluetooth device 146, which provides for wireless personal area networks (PANs). Optical distance sensor 148 can detect the distance from a device to various objects, such as users of the system, while digital camera 150 can be used to capture images of objects, such as users of the system, to enable recognition software, such as facial recognition software, to identify the users of the system. Controller 140 also provides connectivity to other connected devices 142, such as a wearable electronic device band adjustor that adjusts a band that connects the wearable electronic device to a user's arm or other body part, a gyroscope that detects an orientation of the wearable electronic device, and a moisture sensor, such as a hygrometer or galvanometer, that detects a moisture level, such as found in perspiration, found on the user's skin that contacts the wearable electronic device body. GPS receiver 143 is also connected to controller 140 with the GPS receiver receiving location information that pertains to a current location of the wearable electronic device.

Wireless Local Area Network (LAN) device 175 connects to Southbridge 135 via the PCI or PCI Express bus 172. LAN device 175 typically implements one of the IEEE 802.11 standards of over-the-air modulation techniques that all use the same protocol to wireless communicate between information handling system 100 and another computer system or device. Optical storage device 190 connects to Southbridge 135 using Serial ATA (SATA) bus 188. Serial ATA adapters and devices communicate over a high-speed serial link. The Serial ATA bus also connects Southbridge 135 to other forms of storage devices, such as hard disk drives. Audio circuitry 160, such as a sound card, connects to Southbridge 135 via bus 158. Audio circuitry 160 also provides functionality such as audio line-in and optical digital audio in port 162, optical digital output and headphone jack 164, internal speakers 166, and internal microphone 168. Ethernet controller 170 connects to Southbridge 135 using a bus, such as the PCI or PCI Express bus. Ethernet controller 170 connects information handling system 100 to a computer network, such as a Local Area Network (LAN), the Internet, and other public and private computer networks.

While FIG. 1 shows one information handling system, an information handling system may take many forms. For example, an information handling system may take the form of a desktop, server, portable, laptop, notebook, or other form factor computer or data processing system. In addition, an information handling system may take other form factors such as a personal digital assistant (PDA), a gaming device, ATM machine, a portable telephone device, a communication device or other devices that include a processor and memory.

The Trusted Platform Module (TPM 195) shown in FIG. 1 and described herein to provide security functions is but one example of a hardware security module (HSM). Therefore, the TPM described and claimed herein includes any type of HSM including, but not limited to, hardware security devices that conform to the Trusted Computing Groups (TCG) standard, and entitled "Trusted Platform Module (TPM) Specification Version 1.2." The TPM is a hardware security subsystem that may be incorporated into any number of information handling systems, such as those outlined in FIG. 2.

FIG. 2 provides an extension of the information handling system environment shown in FIG. 1 to illustrate that the methods described herein can be performed on a wide variety of information handling systems that operate in a networked environment. Types of information handling systems range from small handheld devices, such as handheld computer/mobile telephone 210 to large mainframe systems, such as mainframe computer 270. Examples of handheld computer 210 include personal digital assistants (PDAs), personal entertainment devices, such as MP3 players, portable televisions, and compact disc players. Other examples of information handling systems include pen, or tablet, computer 220, laptop, or notebook, computer 230, workstation 240, personal computer system 250, and server 260. Other types of information handling systems that are not individually shown in FIG. 2 are represented by information handling system 280. As shown, the various information handling systems can be networked together using computer network 200. Types of computer network that can be used to interconnect the various information handling systems include Local Area Networks (LANs), Wireless Local Area Networks (WLANs), the Internet, the Public Switched Telephone Network (PSTN), other wireless networks, and any other network topology that can be used to interconnect the information handling systems. Many of the information handling systems include nonvolatile data stores, such as hard drives and/or nonvolatile memory. Some of the information handling systems shown in FIG. 2 depicts separate nonvolatile data stores (server 260 utilizes nonvolatile data store 265, mainframe computer 270 utilizes nonvolatile data store 275, and information handling system 280 utilizes nonvolatile data store 285). The nonvolatile data store can be a component that is external to the various information handling systems or can be internal to one of the information handling systems. In addition, removable nonvolatile storage device 145 can be shared among two or more information handling systems using various techniques, such as connecting the removable nonvolatile storage device 145 to a USB port or other connector of the information handling systems.

Figure 3:
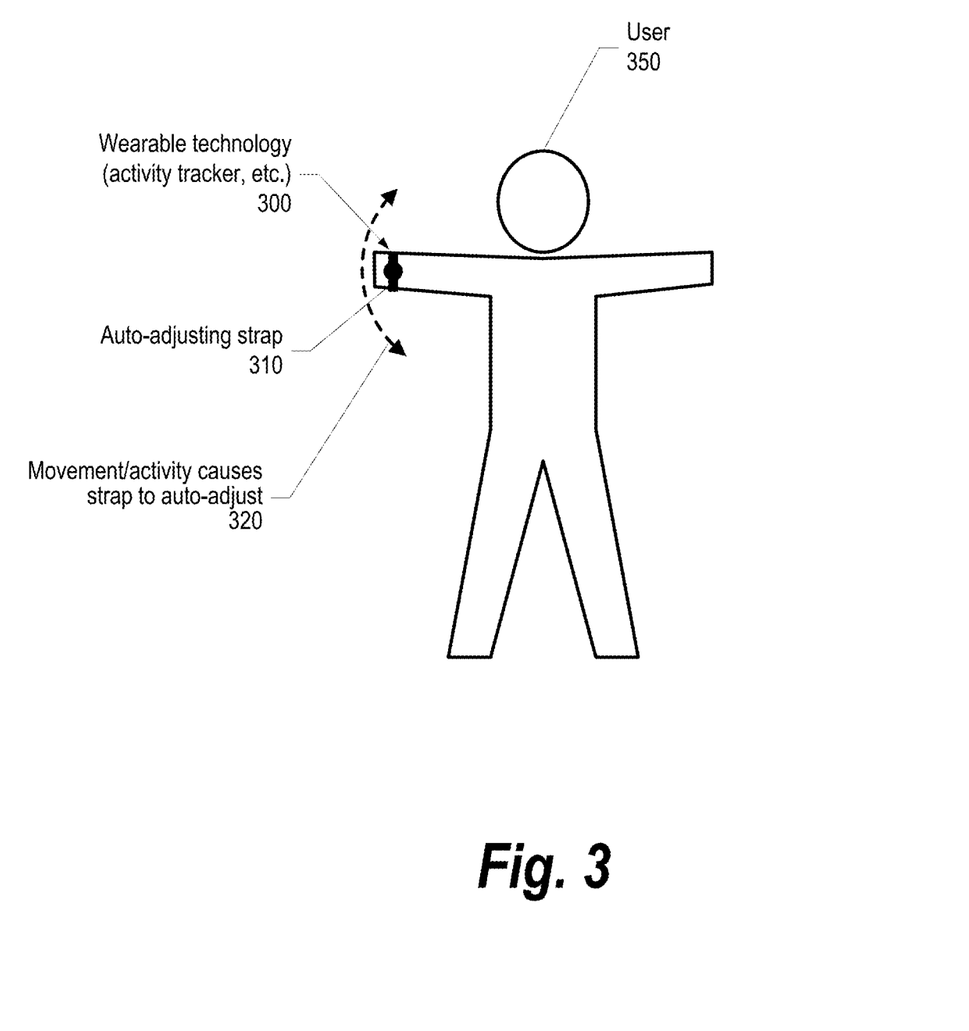
FIG. 3 is a diagram depicting a user wearing a device that has an automatically adjusting strap based on the user's movements.

FIG. 3 is a diagram depicting a user wearing a device that has an automatically adjusting strap based on the user's movements. Wearable electronic device 300, such as an activity tracker or the like, is worn by user 350 by attaching device 300 to a body part of user 350, such as a wrist, using automatic adjusting band 310. Conditions are detected at wearable electronic device 300, such as movement or activity being performed by user 350 as well as a current or predicted location of the wearable electronic device that might indicate that the user is about to perform a particular activity, such as when the user approaches a tennis court to play a game of tennis. Automatic adjustment of the band occurs at 320 in response to the detection of such conditions, such as an activity based condition such as the user moving an arm to a vertical position, and/or a location-based condition such as the user entering a tennis court.

Figure 4:
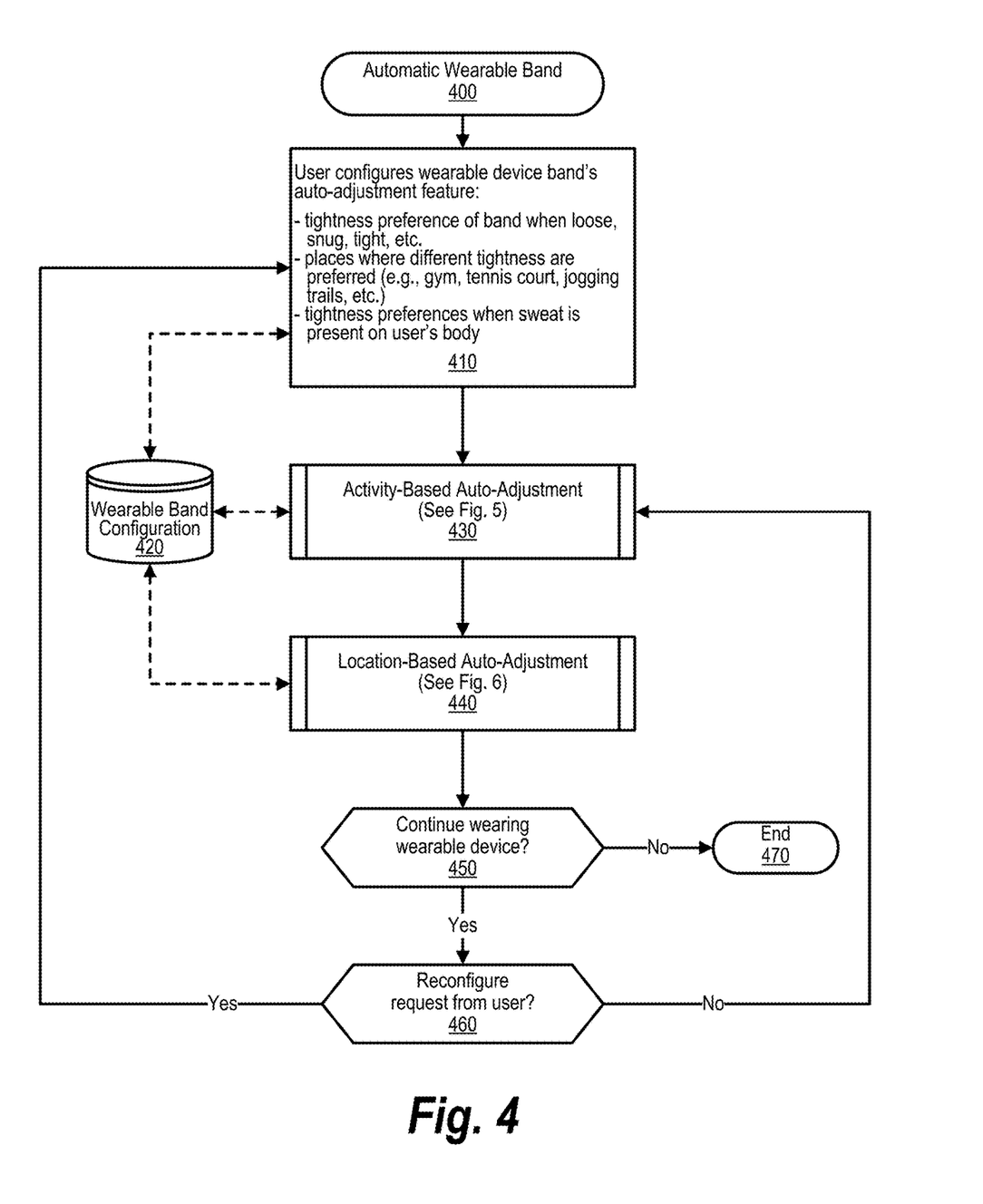
FIG. 4 is a flowchart showing steps performed during usage of a wearable device with an automatically adjusting band.

FIG. 4 is a flowchart showing steps performed during usage of a wearable device with an automatically adjusting band. FIG. 4 processing commences at 400 and shows the steps taken by a process that manages a wearable electronic device and automatically adjusts a band that attaches the wearable electronic device to a user. At step 410, the user configures the wearable electronic device band's auto-adjustment feature. During configuration, the user can indicate a tightness preference of the band when the device is loose, snug, tight, etc. In addition, the user can also configure locations, or places, where different tightness of the automatically adjustable band are preferred. For example, when the user is at the gym, at a tennis court, on a jogging trail, etc. Furthermore, the user can configure tightness preferences for when moisture, such as perspiration, is present on user's body and detected at the wearable electronic device. The configured preferences are stored in data store 420.

Figure 5:
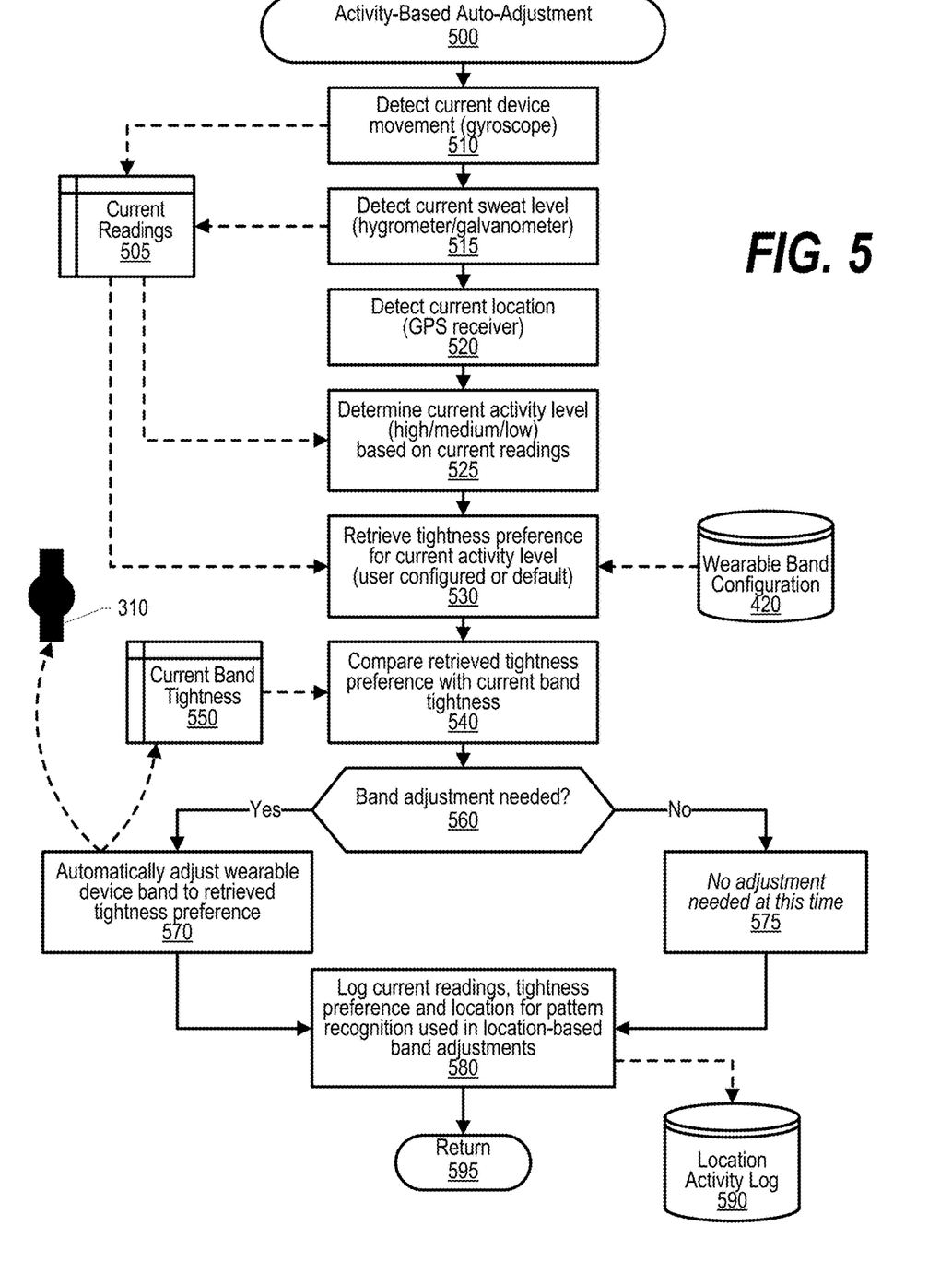
FIG. 5 is a flowchart showing more detailed steps performed to automatically adjust the device band in response to user activity.

At predefined process 430, the process performs the Activity-Based Auto-Adjustment routine (see FIG. 5 and corresponding text for processing details). This routine automatically adjusts the wearable electronic device's band based on the user's activities with the tightness preferences being retrieved from data store 420. At predefined process 440, the process performs the Location-Based Auto-Adjustment routine (see FIG. 6 and corresponding text for processing details). This routine automatically adjusts the wearable electronic device's band based on the user's current or predicted location, such as a tennis court, and uses location-based tightness preferences that are retrieved from data store 420. The process determines as to whether the user continues wearing the wearable electronic device (decision 450). If the user continues wearing the wearable electronic device, then decision 450 branches to the 'yes' branch which continues processing conditions received at the wearable electronic device. Processing continues until the user is no longer wearing the wearable electronic device, at which point decision 450 branches to the 'no' branch exiting the loop and processing ends at 470.

The process determines as to whether a request to reconfigure the wearable electronic device has been received from the user (decision 460). If a request to reconfigure the wearable electronic device has been received from the user, then decision 460 branches to the 'yes' branch which loops back to step 410 to receive the user's configuration updates. On the other hand, if a request to reconfigure the wearable electronic device has not been received from the user, then decision 460 branches to the 'no' branch whereupon processing loops back to predefined process 430 to continue receiving conditions at the wearable electronic device and automatically adjusting the wearable electronic device.

FIG. 5 is a flowchart showing more detailed steps performed to automatically adjust the device band in response to user activity. FIG. 5 processing commences at 500 and shows the steps taken by a process that performs activity-based automatic adjustment of a wearable electronic device's band. At step 510, the process detects any current device movement at the wearable electronic device (e.g., using a gyroscope, etc.). The data received from the sensor(s) performing step 510 is stored in memory area 505. At step 515, the process detects a current moisture level at the wearable electronic device (e.g., using a hygrometer, galvanometer, etc.). The data received from the sensor(s) performing step 515 is stored in memory area 505. At step 520, the process detects a current location of the wearable electronic device (e.g., using a GPS receiver, etc.). The data received from the sensor(s) performing step 520 is stored in memory area 505.

At step 525, the process determines current activity level (e.g., high/medium/low, etc.) based on current readings. Step 525 can also determine an orientation of the wearable electronic device, such as if the device is in a vertical orientation with the user's arm extended upwards (perpendicular to the ground) or is in horizontal orientation with the user's arm extended outwards (parallel to the ground). At step 530, the process retrieves the tightness preferences for the current activity level and device orientation from memory area 505. The band tightness preferences might be user configured or can be default values if the user has not specified such preferences. The user's preferences are retrieved from data store 420. At step 540, the process compares the retrieved tightness preferences with the current band tightness with the current band tightness being retrieved from memory area 550.

The process determines as to whether the wearable electronic device's band needs an adjustment based on the comparison (decision 560). If the wearable electronic device's band needs an adjustment, then decision 560 branches to the 'yes' branch to perform step 570. On the other hand, if the wearable electronic device's band does not need to be adjusted, then decision 560 branches to the 'no' branch whereupon step 575 indicates that no band adjustment is made at this time. At step 570, when a band adjustment is needed, the process automatically adjusts the wearable electronic device's band to the retrieved tightness preference. The current band tightness value is stored in memory area 550 and band 310 is adjusted accordingly.

At step 580, the process logs, or records, the current readings, tightness preference and location for pattern recognition used in location-based band adjustments. The data recorded at step 580 is stored in data store 590. FIG. 5 processing thereafter returns to the calling routine (see FIG. 4) at 595.

Figure 6:
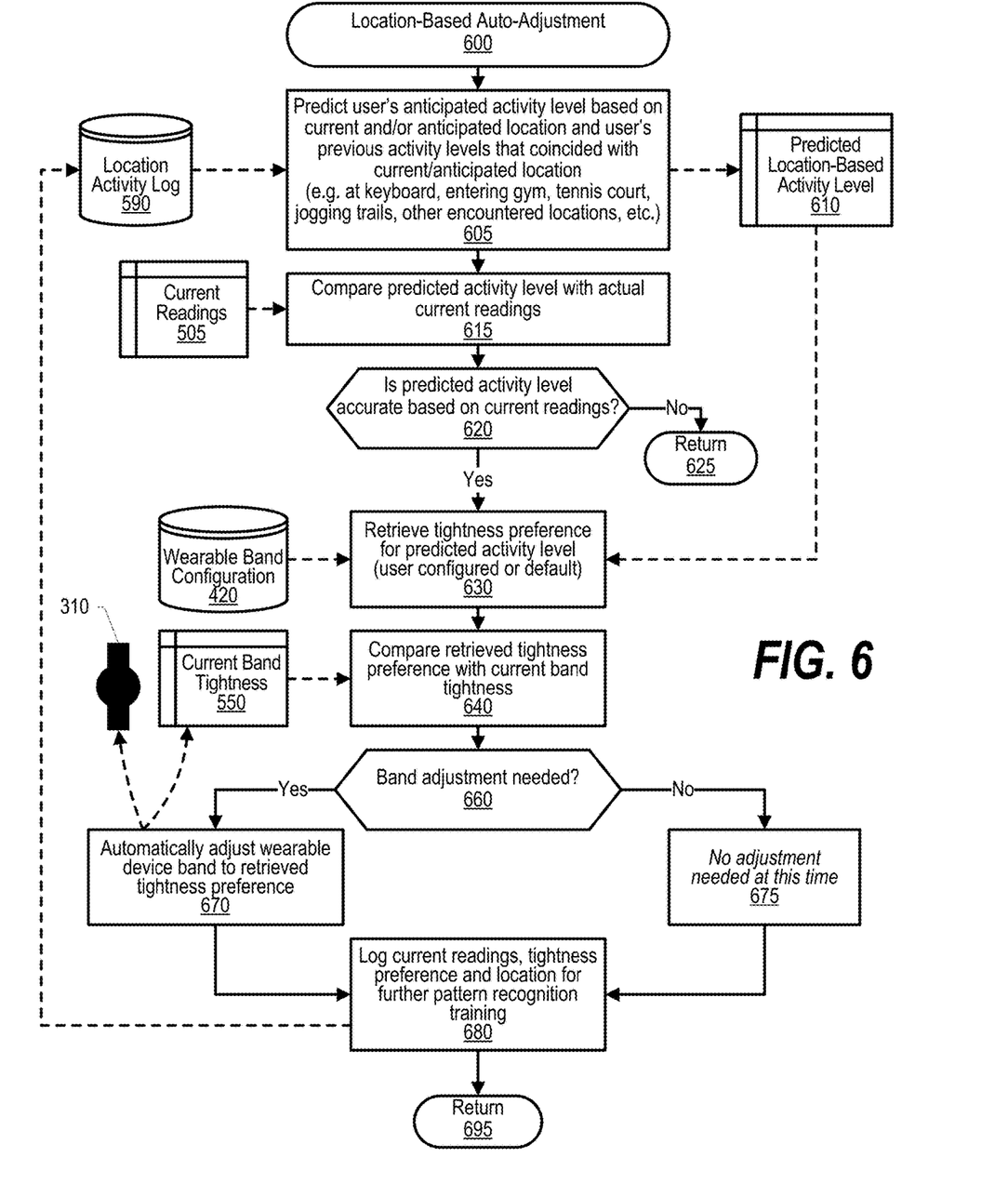
FIG. 6 is a flowchart showing steps performed to automatically adjust a device band based on a current location of the user.

FIG. 6 is a flowchart showing steps performed to automatically adjust a device band based on a current location of the user. FIG. 6 processing commences at 600 and shows the steps taken by a process that location-Based Auto-Adjustment. At step 605, the process predicts the user's anticipated activity level based on the user's current and/or anticipated location and the user's previous activity levels that coincided with the current/anticipated location (e.g. the user being at a keyboard, entering a gym, approaching tennis court, on a jogging trail, or other encountered locations, etc.). The prediction is based on the user's previous activities and locations that were recorded in data store 590. The result of step 605 is a predicted location-based activity level that is stored in memory area 610.

At step 615, the process compares the predicted activity level stored in memory area 610 with the actual current readings from the wearable electronic device that are retrieved from memory area 505. The process determines whether the comparison reveals that the predicted activity level is accurate based on the current readings from the wearable electronic device (decision 620). If the predicted activity level is accurate, then decision 620 branches to the 'yes' branch for further processing of the location-based adjustment. On the other hand, if the predicted activity level is not found to be accurate, then decision 620 branches to the 'no' branch whereupon processing thereafter to the calling routine (see FIG. 4) at 625.

At step 630, the process retrieves the user's tightness preference for the predicted activity level (user configured or default). The tightness level is retrieved from data store 420. At step 640, the process compares the retrieved tightness preference with the current band tightness that is retrieved from memory area 550. Based on the comparison, the process determines whether an adjustment to the wearable electronic device's band adjustment is currently needed (decision 660). If a band adjustment is currently needed, then decision 660 branches to the 'yes' branch whereupon, at step 670, an adjustment to band 310 is automatically made to the tightness preference retrieved at step 630 and the current band adjustment value is updated in memory area 550. On the other hand, if no band adjustment needed, then decision 660 branches to the 'no' branch whereupon, as shown in 675, no band adjustment is made at this time.

At step 680, the process logs the current wearable electronic device readings, the tightness preference and the current location for further pattern recognition training. This data is stored in data store 590. FIG. 6 processing thereafter returns to the calling routine (see FIG. 4) at 625.

While particular embodiments have been shown and described, it will be obvious to those skilled in the art that, based upon the teachings herein, that changes and modifications may be made without departing from this invention and its broader aspects. Therefore, the appended claims are to encompass within their scope all such changes and modifications as are within the true spirit and scope of this invention. Furthermore, it is to be understood that the invention is solely defined by the appended claims. It will be understood by those with skill in the art that if a specific number of an introduced claim element is intended, such intent will be explicitly recited in the claim, and in the absence of such recitation no such limitation is present. For non-limiting example, as an aid to understanding, the following appended claims contain usage of the introductory phrases "at least one" and "one or more" to introduce claim elements. However, the use of such phrases should not be construed to imply that the introduction of a claim element by the indefinite articles "a" or "an" limits any particular claim containing such introduced claim element to inventions containing only one such element, even when the same claim includes the introductory phrases "one or more" or "at least one" and indefinite articles such as "a" or "an"; the same holds true for the use in the claims of definite articles.

What is claimed is:

1. A method comprising:
   identifying one or more conditions pertaining to a wearable electronic device that includes an adjustable band;
   detecting an orientation of the wearable electronic device, wherein the orientation is in respect to the ground;
   automatically adjusting the adjustable band based on the detected orientation of the wearable electronic device, wherein the adjusting further comprises:
      tightening the adjustable band in response to the detected orientation being a vertical orientation; and
      loosening the adjustable band in response to the detected orientation being a horizontal orientation.

2. The method of claim 1 wherein one of the conditions is an activity-based condition, and wherein the method further comprises:
   detecting a movement of the wearable electronic device; and
   automatically adjusting the adjustable band based on the detected movement of the wearable electronic device.

3. The method of claim 1 wherein one of the conditions is a location-based condition, and wherein the method further comprises:
   identifying a location of the wearable electronic device;
   determining a predicted activity level at the identified location;
   automatically adjusting the adjustable band based on the predicted activity level.

4. The method of claim 3 further comprising:
   identifying a current location of the wearable electronic device;
   determining an anticipated future location of the wearable electronic device based on the current location, wherein the identified current location is the anticipated future location.

5. A wearable electronic device comprising:
   a device body;
   an adjustable band connected to the device body;
   one or more processors within the device body;
   a memory coupled to at least one of the processors and also within the device body; and
   a set of instructions stored in the memory and executable by at least one of the processors to:
      identify one or more conditions pertaining to the wearable electronic device that includes the adjustable band;
      detect an orientation of the wearable electronic device, wherein the orientation is in respect to the ground;
      automatically adjust the adjustable band based on the detected orientation of the wearable electronic device, wherein the adjusting further comprises instructions that are further executable to:
         tighten the adjustable band in response to the detected orientation being a vertical orientation; and
         loosen the adjustable band in response to the detected orientation being a horizontal orientation.

6. The wearable electronic device of claim 5 wherein one of the conditions is an activity-based condition, and comprising instructions that are further executable to:
   detect a movement of the wearable electronic device; and
   automatically adjust the adjustable band based on the detected movement of the wearable electronic device.

7. The wearable electronic device of claim 5 wherein one of the conditions is a location-based condition, and comprising instructions that are further executable to:
   identify a location of the wearable electronic device;
   determine a predicted activity level at the identified location;
   automatically adjust the adjustable band based on the predicted activity level.

8. The wearable electronic device of claim 7 further comprising instructions that are further executable to:
   identify a current location of the wearable electronic device;
   determine an anticipated future location of the wearable electronic device based on the current location, wherein the identified current location is the anticipated future location.

9. A computer program product comprising:
a computer readable storage medium comprising a set of computer instructions, the computer instructions effective to:
identify one or more conditions pertaining to a wearable electronic device that includes an adjustable band;
detect an orientation of the wearable electronic device, wherein the orientation is in respect to the ground;
automatically adjust the adjustable band based on the detected orientation of the wearable electronic device, wherein the adjusting further comprises instructions that are further executable to:
tighten the adjustable band in response to the detected orientation being a vertical orientation; and
loosen the adjustable band in response to the detected orientation being a horizontal orientation.

10. The computer program product of claim 9 wherein one of the conditions is an activity-based condition, and comprising computer instructions that are further effective to:
detect a movement of the wearable electronic device; and
automatically adjust the adjustable band.

11. The computer program product of claim 9 wherein one of the conditions is a location-based condition, and comprising computer instructions that are further effective to:
identify a location of the wearable electronic device;
determine a predicted activity level at the identified location;
automatically adjust the adjustable band based on the predicted activity level.

* * * * *